United States Patent
Wood et al.

(10) Patent No.: US 8,663,314 B2
(45) Date of Patent: *Mar. 4, 2014

(54) CONTINUOUS DOUBLE LAYERED STENT FOR MIGRATION RESISTANCE

(75) Inventors: Mark Wood, Shrewsburg, MA (US); Paul Norton, Lunenburg, MA (US); William Bertolino, Framingham, MA (US); F. Anthony Headley, Jr., Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 40 days.

This patent is subject to a terminal disclaimer.

(21) Appl. No.: 13/396,088

(22) Filed: Feb. 14, 2012

(65) Prior Publication Data

US 2012/0150277 A1 Jun. 14, 2012

Related U.S. Application Data

(63) Continuation of application No. 12/483,488, filed on Jun. 12, 2009, now Pat. No. 8,114,147.

(60) Provisional application No. 61/061,800, filed on Jun. 16, 2008.

(51) Int. Cl.
*A61F 2/82* (2013.01)

(52) U.S. Cl.
USPC ............................................. 623/1.15

(58) Field of Classification Search
USPC ................................................ 623/1.15–1.48
See application file for complete search history.

(56) References Cited

U.S. PATENT DOCUMENTS

| | | | |
|---|---|---|---|
| 5,776,141 A | 7/1998 | Klein et al. | |
| 6,290,721 B1 | 9/2001 | Heath | |
| 6,357,104 B1 | 3/2002 | Myers | |
| 6,607,552 B1 | 8/2003 | Hanson | |
| 6,866,679 B2 | 3/2005 | Kusleika | |
| 7,011,678 B2 | 3/2006 | Tenerz et al. | |
| 7,462,192 B2 | 12/2008 | Norton et al. | |
| 7,588,597 B2 | 9/2009 | Frid | |
| 7,780,725 B2 | 8/2010 | Haug et al. | |
| 8,114,147 B2 * | 2/2012 | Wood et al. | 623/1.15 |
| 8,303,650 B2 * | 11/2012 | Shokoohi | 623/1.42 |
| 2008/0281398 A1 | 11/2008 | Koss et al. | |
| 2009/0088832 A1 | 4/2009 | Chew et al. | |
| 2009/0248135 A1 | 10/2009 | Bruszewski et al. | |
| 2009/0270971 A1 | 10/2009 | Xiao et al. | |
| 2010/0042136 A1 | 2/2010 | Berrada et al. | |
| 2010/0204772 A1 | 8/2010 | Holzer et al. | |
| 2013/0060327 A1 * | 3/2013 | Shokoohi et al. | 623/1.42 |

* cited by examiner

*Primary Examiner* — Suzette J Gherbi
(74) *Attorney, Agent, or Firm* — Vidas, Arrett & Steinkraus

(57) ABSTRACT

The present invention relates to stent structures having improved migration resistance. In particular, the invention relates to mesh stents, such as braided or twisted stent designs, where at least a portion of the stent is folded back over itself to form a multi-layered stent device. Such multi-layered portions provide for migration resistance, among other advantages.

16 Claims, 5 Drawing Sheets

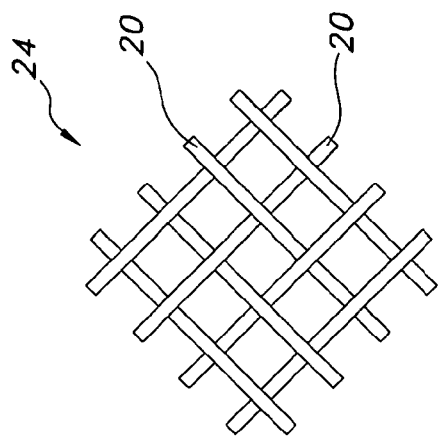
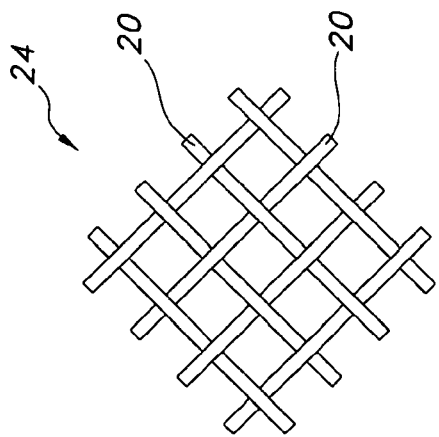
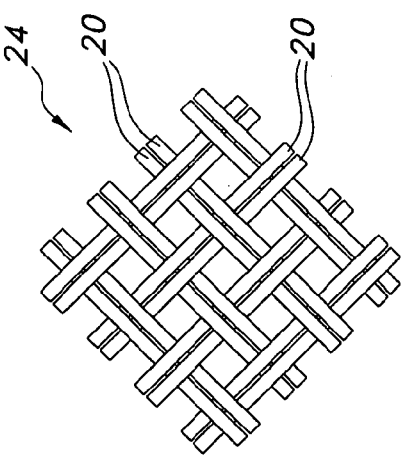
FIG. 2A
FIG. 2B
FIG. 2C

CONTINUOUS DOUBLE LAYERED STENT FOR MIGRATION RESISTANCE

CROSS-REFERENCE TO RELATED APPLICATIONS

The present invention is a continuation of U.S. patent application Ser. No. 12/483,488, filed on Jun. 12, 2009, is a non-provisional conversion of U.S. Patent Application Ser. No. 61/061,800, filed on Jun. 16, 2008, the entire contents of which are incorporated herein by reference.

FIELD OF THE INVENTION

The present invention relates to stent structures having improved migration resistance. In particular, the invention relates to mesh stents, such as braided stent designs, where at least a portion of the stent is folded back over itself to form a dual-layered stent device. Such dual-layered portions provide for migration resistance, among other advantages.

BACKGROUND OF THE INVENTION

An intraluminary prosthesis, for example a stent, is a medical device used in the treatment of diseased bodily lumens. A stent is generally a longitudinal tubular device formed of biocompatible material which is useful to open and support various lumens in the body. For example, stents may be used in the bodily vessel, such as in the coronary or peripheral vasculature, esophagus, trachea, bronchi colon, biliary tract, urinary tract, prostate, brain, as well as in a variety of other applications in the body.

A stent generally includes an open flexible configuration which allows the stent to be configured in a radially compressed state for intraluminary catheter implantation. Once properly positioned adjacent the target body lumen, the stent is radially expanded so as to support and reinforce the vessel. Radial expansion of the stent may be accomplished by inflation of a balloon attached to the catheter or the stent may be of the self-expanding variety which will radially expand once deployed. Balloon expandable and self-expanding stents are known. Such self-expandable stents in use include those in the Applicant's WallFlex® stent family, including the WallFlex® Enteral, Esophageal and Biliary stent designs.

To prevent migration of the stent after implantation, the stent is anchored to the inner wall of the lumen. On occasion, however, it may be necessary after implantation to remove a stent that is anchored to the body lumen or to shift the placement of the stent after implantation. However, in current stent devices, due to the anchoring of the stent to the inside wall of the body lumen, such removal or shifting may be difficult, if not impossible.

Thus, there is a need for a stent or intraluminal prosthesis which provides improved migration resistance, as well as allowing for easy in vivo adjustment and/or removal of the stent. The present invention meets these needs and provides advantages beyond those known in the art.

SUMMARY OF THE INVENTION

The present invention incorporates a continuous dual-layered stent device, which allows for sufficient anchoring while reducing the risk of migration, and additionally allows for shifting and/or removal of the stent after implantation.

In another embodiment of the invention, there is provided a stent including a stent body, which has a cylindrical mesh segment, the cylindrical mesh segment formed from at least one wire, where the wire forms a plurality of intersecting crossing points to define an open lattice tubular wall; and at least a portion of the open lattice tubular wall is inverted upon itself to form a dual layered cylindrical mesh segment. Desirably the plurality of intersecting points from a braid or braided section(s). Desirably the stent is made from 8 to 24 wires.

In one embodiment of the invention, there is provided a generally tubular stent, which includes: an inner braided section and a concentric outer braided section, where the outer braided section forms a continuous braid with the inner braided section. Both the inner and outer braided section includes at least one wire, which has intersecting crossing points to define the braided section.

In another embodiment, there is provided a method of implanting a tubular stent including the steps of: implanting a stent, wherein the stent comprises: a first stent body having a generally cylindrical mesh segment, the mesh segment formed from at least one first wire, and the first wire forming a plurality of intersecting crossing points to define an open lattice tubular wall; and implanting a second stent, wherein the stent includes: a second stent body having a generally cylindrical mesh segment, the mesh segment formed from at least one second wire, and the second wire forming a plurality of intersecting crossing points to define an open lattice tubular wall; and at least partially connecting an end of the first stent body to an end of the second stent body to form a multi-layered stent.

BRIEF DESCRIPTION OF THE DRAWINGS

FIG. 2A is an exploded view of a stent of the present invention illustrating a one-under and one-over braiding configuration.

FIG. 2B is an exploded view of a stent of the present invention illustrating a two-under and two-over braiding configuration.

FIG. 2C is an exploded view of a stent of the present invention illustrating a pair of filaments in a one-under and one-over braiding configuration.

DETAILED DESCRIPTION OF THE INVENTION

Devices having improved migration resistance, as well as other advantages, are provided. The devices and assemblies may be suited for various medical applications, and particularly, minimally invasive or intraluminal applications, in various bodily lumens, including but not limited to the gastrointestinal tract, the biliary tract, the urinary tract, and the respiratory tract. Further, the assembly in accordance with the present invention could also be used in the neurological system (e.g., in the brain) and in the cardiovascular system (e.g., in the heart). Reference to bodily passageways may be to passageways in any of the aforementioned tracts and systems or elsewhere in the body, including fabricated lumens or openings.

While the present invention may be applied to the delivery of many intraluminary devices, it is particularly suited for stents, and more particularly of self-expanding stents. Such stents and delivery systems for the stents are generally known in the art. Those stents particularly useful in the present invention are capable of being radially compressed and longitudinally extended for implantation into the bodily lumen. The degree of elongation and the diameter of the stent may be quite varied, depending upon the desired lumen in which the stent is to be implanted. It is particularly desirable that the stent be constructed to self-expand when released from a radially compressed state, for example during deployment.

Figure 1:
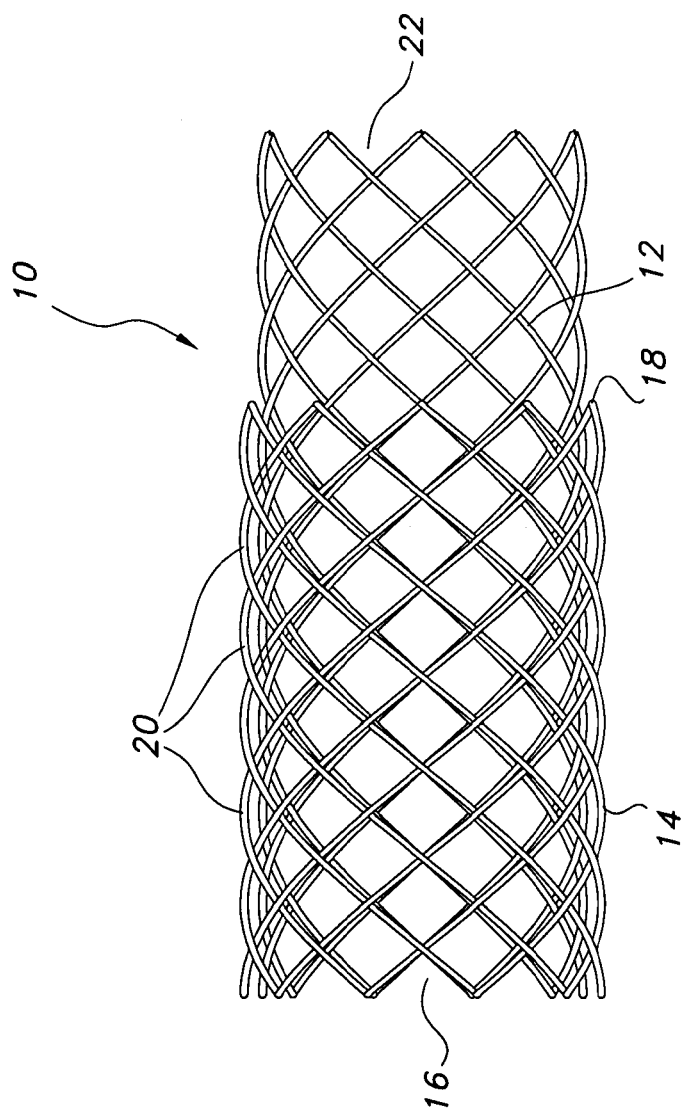
FIG. 1 illustrates an embodiment of the present invention showing the double braided stent device.

With reference to FIG. 1, one embodiment of the stent device 10 of the present invention is provided. The stent 10 is a hollow, generally cylindrical mesh structure, having two axially opposite open ends 16 and 22. The structure of the stent 10 includes a series of wires or filaments 20, which preferably extend at least a majority of the length of the stent 10, and most preferably the entire length of the stent 10.

Figure 5:
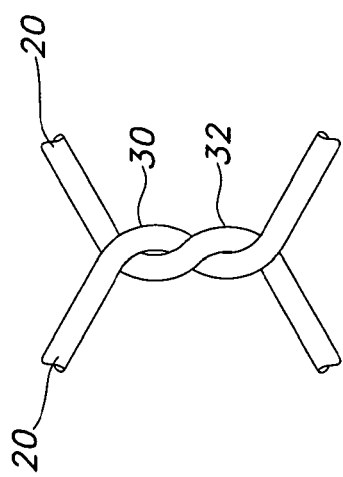
FIG. 5 illustrates an embodiment of the present invention incorporating a twisted configuration of filaments.

The filaments 20 are preferably elastic shape-memory alloy wires, for example, those made from superelastic materials such as nitinol, and most preferably the type which allow for self-expansion. Other materials may include shape memory polymers or metals, or simply elastic materials. Further, materials may also include plastically expandable materials. The filaments 20 preferably form an open lattice tubular wall. In one preferred embodiment, the filaments 20 are continuously woven together in a braided form, as will be described in more detail below. The structure is not limited to woven structures, and includes other such fabrications as knitting, braiding, crocheting, welding, suturing, tying, or other such methods of producing interconnected structures. FIG. 5 depicts one such alternate structure, which uses a twisted structure. In a twisted structure, the filaments 20 are twisted around each other at least one time. There may be multiple twists at each twist location. FIG. 5 depicts a dual-twist structure, having two twists 28 and 30 at each twist location.

In a preferred embodiment, the stent 10 includes at least two mesh segments, in particular an inner segment 12 and an outer segment 14. The two segments 12 and 14 are preferably hollow, generally cylindrical bodies, and are formed of mesh filaments 20. The two segments 12 and 14 may be different in structure, manufacture, size or design. For example, one may be braided, while another may be crocheted, or one segment may have layer cells, while the other does not. In addition, the two segments 12 and 14 may be made from different materials or they may be made from the same materials. The inner segment 12 and the outer segment 14 are preferably disposed concentrically, with the outer segment 14 being located on the outside surface of the inner segment 12. The two segments 12 and 14 are desirably formed from the same continuously interconnected mesh structure, and may be formed for example by forming a first segment of a stent body 10 and inverting one end of the stent body 10 back upon itself to form a multi-layered, generally cylindrical mesh segment. In one embodiment, the mesh segment includes two layers. Of course, the two segments 12 and 14 may not be made from the same continuously interconnected structure, and may be attached by a friction fit or other non-permanent fits. The outer segment 14 may cover the entire length of the inner segment 12, or it may cover only a portion of the inner segment 12. In an alternative embodiment, the outer section 14 may extend beyond the length of the inner segment 12. There may be one or more additional layers, such as other stents, coatings or liners, disposed between the inner segment 12 and the outer segment 14, or the segments 12 and 14 may be disposed directly on each other. Either inner, outer, or both segments may be coated or covered, and may have the same or varying mechanical properties. Use of a double layered stent configuration provides superior anti-migration abilities.

The use of the multiple layer design aids in anchoring the stent 10 to the implant site, and further aids in the removal of the stent 10 if the need arises. In addition, the use of the multi-layered design allows for repositioning of the stent 10 even after it has been implanted. The multiple layer design may also aid in self-sizing of the stent 10. For example, the stent 10 may include a self-sized area disposed between the inner and outer segments 12 and 14, so that the user may move the layers with respect to each other but not the self sized area.

Braiding of the filaments 20 may be accomplished by any desired means. One such preferred braiding means is through the use of a braiding mandrel, although any desired braiding means may be used. For example, such stents 10 may be braided via the use of braiding mandrels having specifically designed grooves and detents and constant force braiding carriers for tangentially delivering filaments 20 for braiding the filaments 20 onto such specifically designed mandrels. The braiding angle throughout the stent 10 preferably is substantially constant, although there may be slight differences in the angle between the inner segment 12 and the outer segment 14. The braiding angle is preferably between about 90° to about 130°, and most preferably is between 100° to 120°. Further, other regions, such as flared or tapered ends, may have different angles than the rest of the stent 10. For example, in one embodiment, the braiding angle may be about 110°±3°, desirably about 110°±1°. In some embodiments, the present invention may avoid undesirable variations through the use of such components as, inter alia, constant force carriers, constant force bobbin carriers, using a braiding mandrel having raised projections, and/or stent-filament-holding detents on the mandrel. In some embodiments, the braiding angle may be varied throughout the length of the stent 10.

The braiding of the filaments 20 may be arranged in any number of acceptable ways. Several suitable braiding configurations are depicted in FIGS. 2A-2C, which are exploded views 24 of the stent 10 of FIG. 1. For example, the braiding may be "one-under and one-over" style. The one-under and one-over braiding configuration is depicted in an exploded view in FIG. 2A. In this embodiment, the braiding arrangement includes filaments 20 which alternate in a braiding pattern having a 1/1 intersection, i.e., one-under and one-over pattern. The stent 10, however, is not limited to any specific braiding pattern. As depicted by the exploded view 24 in FIG. 2B, the braiding arrangement may include the filaments 20 braided in a two-under and a two-over pattern. Further, as illustrated in FIG. 2C, the braiding arrangement may be accomplished by using a pair of filaments 20' in a one-under and one-over pattern. The pair of filaments 20' may be the same or may be different, i.e., may have the same or different dimensions, shapes and/or materials of construction. Moreover, the pair of filaments 20' may suitably be braided in other braided patterns, such as but not limited to, for example, the two-under and two-over pattern described above. Other braiding patterns known in the art may also be suitably be used. Some portions of the mesh segments may be non-interlocking if desired, including such designs as inter-twisting, inter-looping, inter-engaging and the like at the intersection of the braided filaments 20, 20'. Other braiding patterns include those described in U.S. Pat. No. 5,800,519 to Sandock, the contents of which are incorporated herein by reference.

In one embodiment, the inner segment 12 and the outer segment 14 are connected together in one continuous piece, where the outer segment 14 is inverted or folded over the inner segment 12. Thus, some of the filaments 20 of the inner segment 12 are common to some of the filaments 20 of the outer segment 14. In an alternative embodiment, the inner segment 12 and the outer segment 14 may be looped together at one end of the stent 10. For example, the mesh segments of one end of the inner segment 12 may be engaged with or locked with mesh segments of one end of the outer segment 14.

As used herein, the term "inverted end" will refer to the location where the outer segment 14 is folded over or looped with the inner segment 12. The inverted end 16 may form one open end of the tubular stent 10. By "inverted end" it is to be understood that the end is not limited to one particular embodiment wherein the stent 10 is inverted over itself. Rather, the term "inverted end" also includes embodiments incorporating two separate segments 12 and 14, which may be connected or looped at the "inverted end" 16.

The open end of the stent 10 located axially opposite the inverted end 16 will be referred to herein as the "distal end" 22, and may be any shape or pattern desired. The distal end 22 may include a flared end, a barbed end, or any atraumatic end desired, or alternatively, it may simply be an open end. For example, the distal end 22 may be formed by bending the filaments 20 at or about the middle portion of the length of the filaments 20 to form bends and beginning the braid at this end. Alternatively, the distal end 22 may have its wire(s) or filament(s) 20 welded or looped to form an atraumatic end. Either or both of the ends 16 and 22 of the stent 10 may have atraumatic ends. Thus, the stent 10 as implanted is a generally cylindrical, hollow tubular structure having two axially opposed open ends. In this embodiment, one open end is the inverted end 16, and the other open end is the distal end 22, which may also optionally have an inverted end, a flared end or a flared inverted end. The ends may be the same, or they may be different.

In an alternate embodiment, both ends of the stent 10 may include an inverted end 16, which includes the inner segment 12 and the outer segment 14, which outer segment 14 has been inverted over the inner segment 12. In this embodiment, there will be two outer segments 14, inverted over the inner segment 12. The stent 10 may be inverted on itself more than one time, for example, it may have any number of desired layers. More layers may help the stent 10 in overall anchoring, i.e., by preventing migration once it has been implanted.

As used herein, the term "free end" 18 refers to the end of the outer segment 14, which has been inverted over the inner segment 12. The free end 18 of the outer segment 14 may be attached to the inner segment 12, or alternatively it may be left unattached to the inner segment 12. Attachment may be made by any means desired, including looping, weaving, adhering, suturing or other desired attachment. In another embodiment, the free end 18 of the outer segment 14 may be attached to itself to form loops. The free end 18 of the outer segment 14 may be located approximately at the same location as the distal end 22 of the stent 10, or alternatively it may be located axially closer to the inverted end 16. Further, in one embodiment, the free end 18 may extend axially beyond the distal end 22.

Figure 3:
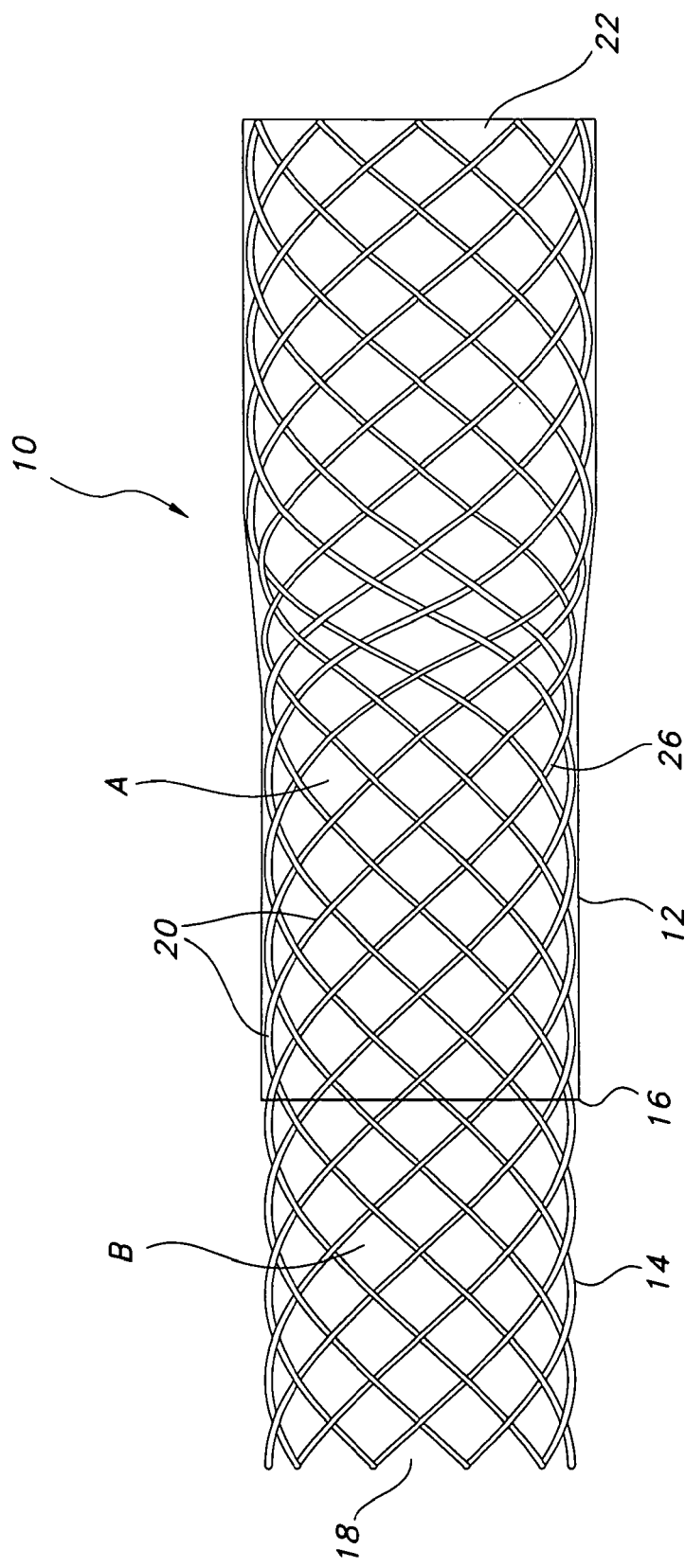
FIG. 3 illustrates an embodiment of the present invention, prior to the outer segment being folded over the inner segment.
Figure 4:
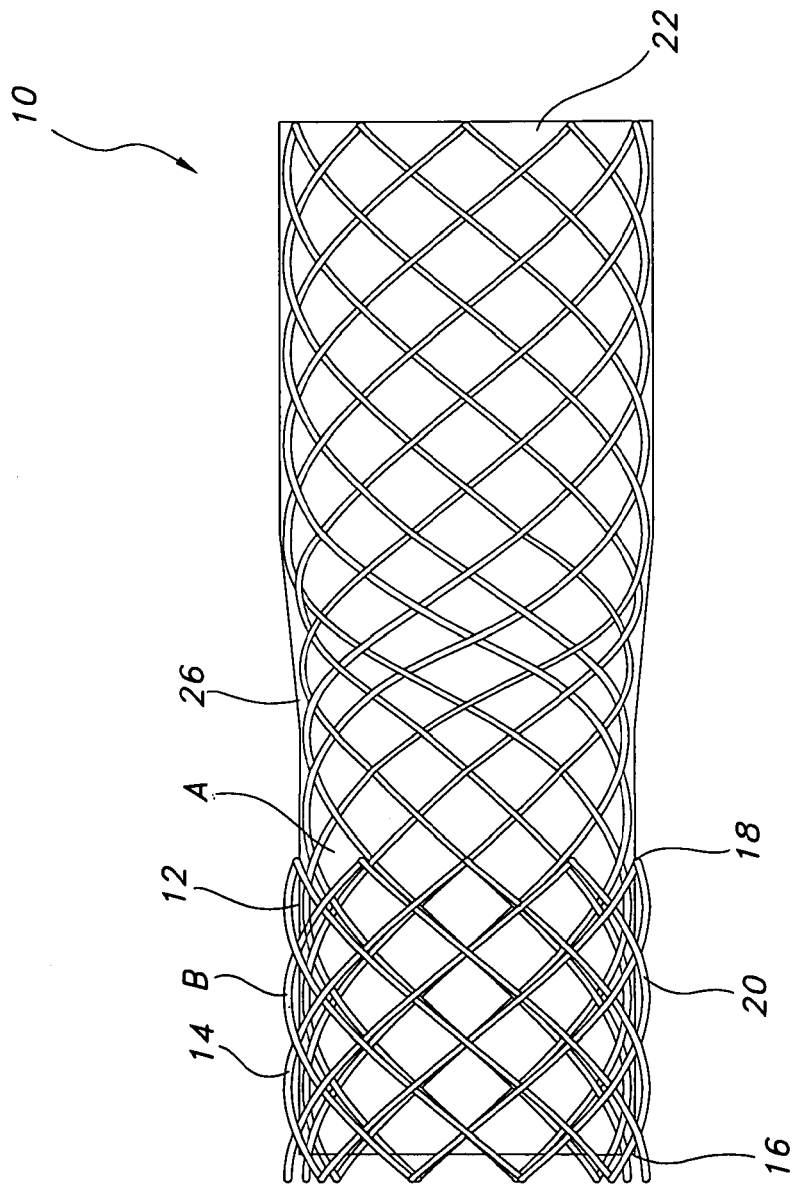
FIG. 4 illustrates the embodiment of FIG. 3, after the outer segment has been folded over the inner segment.

Referring to FIGS. 3 and 4, an embodiment in which the outer segment 14 is folded over the inner segment 12 is illustrated. To demonstrate the full effect of folding the stent 10 over itself, the outer segment 14 is labeled with the letter "B", and the inner segment 12 is labeled with the letter "A". FIG. 3 depicts the stent 10 prior to folding. The unfolded stent 10 includes the inner section 12 and the outer section 14, in an axial arrangement. As can be seen, the unfolded stent 10 is a linear, tubular structure, where the free end 18 of the outer segment 14 is located at one axial end of the stent 10, and the distal end 22 is located at the opposite axial end of the stent 10. Both segments 12 and 14 include a series of braided filaments 20. The braided filaments 20 may be continuous throughout the stent 10 or they may be individual filaments 20 attached or adhered to each other.

FIG. 4 illustrates the stent 10 of FIG. 3, after the outer segment 14 has been folded over the inner segment 12. As can be seen, the free end 18 of the outer segment 14 is now located at a location axially closer to the distal end 22 of the stent 10. The inverted end 16 now forms the open end of the stent 10 located axially opposite the distal end 22.

In an alternate embodiment, the distal end 22 may be folded over the inner segment 12, forming a dual-folded stent. Optional double layer stent configurations include those disclosed in U.S. Pat. No. 6,264,689 to Colgan et al., the contents of which are incorporated herein by reference.

Thus, the segments 12 and 14 may be formed from two distinct stent bodies, or alternately they may be formed from one continuous body. Optionally, the outer segment 14 may be formed separately and attached to the inner segment 12. Such attachment may be by any means desired, such as by welding or other means including crimping, clipping, or suturing. Alternatively, the segments 12 and 14 may be fitted concentrically and left unattached. In embodiments where the outer segment 14 and the inner segment 12 are made of separate tubular structures, the two segments 12 and 14 are preferably attached to each other by the above means.

Optionally, the distal end 22 or may have portions which have varied diameters, such as tapered portions, flared portions and/or flanged portions. Similarly, the free end 18 may have similar properties or it may be different. As depicted in FIGS. 3 and 4, the distal end 22 is shown as a flared end. Alternatively, the distal end 22 may be tapered, or it may have any number of extending ends, including barbs or other attachment means.

Desirably, the filaments 20 are made from any suitable implantable material, such as metals, plastics, or other materials. However, it is preferred that the filaments 20 be constructed of a biocompatible metal or polymeric material. Such suitable materials include, without limitation nitinol, stainless steel, cobalt-based alloy such as Elgiloy®, platinum, gold, titanium, tantalum, niobium, polymeric materials and combinations thereof. Useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), polyethylene terephthalate (PET), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene)poly(D,L-lactide-co-caprolactone) PLA/PCL), poly(glycolide-co-caprolactone) (PGA/PCL), poly(phosphate ester) and the like. The filaments 20 may include materials made from or derived from natural sources, such as, but not limited to collagen, elastin, glycosaminoglycan, fibronectin and laminin, keratin, alginate, extra cellular matrix, or combinations thereof and the like.

Filaments 20 made from polymeric materials may also include radiopaque materials, such as metallic-based powders, particulates or pastes which may be incorporated into the polymeric material. For example the radiopaque material may be blended with the polymer composition from which the polymeric wire is formed, and subsequently fashioned into the stent as described herein. Alternatively, the radiopaque material may be applied to the surface of the metal or polymer stent. In either embodiment, various radiopaque materials and their salts and derivatives may be used including, without limitation, bismuth, barium and its salts such as barium sulphate, tantalaum, tungsten, gold, platinum and titanium, to name a few. Additional useful radiopaque materials may be found in U.S. Pat. No. 6,626,936, which is herein incorporated in its entirely by reference. Metallic complexes useful as radiopaque materials are also contemplated. The stent may be selectively made radiopaque at desired areas along the wire or made be fully radiopaque, depending on the desired end-product and application. Further, the filaments 20 may have an inner core of tantalum, gold, platinum, iridium or combination of thereof and an outer member or layer of nitinol to provide a composite wire for improved radiocapicity or visibility. Desirably, the inner core is platinum and the outer layer is nitinol. More desirably, the inner core of platinum represents about at least 10% of the wire based on the overall cross-sectional percentage. Moreover, nitinol that has not been treated for shape memory such as by heating, shaping and cooling the nitinol at its martensitic and austenitic phases, is also useful as the outer layer. Further details of such composite wires may be found in U.S. Patent Application Publication 2002/0035396 A1, the contents of which is incorporated herein by reference. Preferably, the filaments 20 are made from nitinol, or a composite wire having a central core of platinum and an outer layer of nitinol.

The materials of the stent 10, as well as the materials forming the filaments 20, may be further enhanced with coverings, films, coatings, and other materials. A covering, film, or coating may be in the form of a tubular structure, or it may be placed directly onto the surface of the filaments 20. The coating may be a substantially continuous layer. The filaments 20 may be covered or may be left bare, or combinations thereof. For example, portions of the stent 10 may include covered filaments 20, while other portions may include bare filaments 20. Further, portions of the filaments 20, such as the portion on the inner (luminal) surface of the stent 10, may be covered.

In one preferred embodiment, the filaments 20 which make up the outer segment 14 may be coated, while the filaments 20 which make up the inner segment 12 may be bare. The coating may be made of any material which is suitable for implantation into the body. Coatings may include any plastic or polymeric material, desirably a hard but flexible plastic material. Alternatively, the coating may be silicone or silicone-like material. Coatings may be applied to the filaments 20 prior to braiding or after the filaments 20 have been braided.

In another optional embodiment, any portion of the stent 10 may be covered with a continuous coating layer, such as a sleeve or liner 26. Alternatively, the stent 10 may be covered with a discontinuous layer across at least a portion of the mesh segment. Such sleeves or liners may alternatively be constructed of other biocompatible materials, including but not limited to polymeric materials, such as polyethylene, polypropylene, polyvinyl chloride, polytetrafluoroethylene, including expanded polytetrafluoroethylene (ePTFE), fluorinated ethylene propylene, fluorinated ethylene propylene, polyvinyl acetate, polystyrene, poly(ethylene terephthalate), naphthalene, dicarboxylate derivatives, such as polyethylene naphthalate, polybutylene naphthalate, polytrimethylene naphthalate and trimethylenediol naphthalate, polyurethane, polyurea, silicone rubbers, polyamides, polyimides, polycarbonates, polyaldehydes, polyether ether ketone, natural rubbers, polyester copolymers, styrene-butadiene copolymers, polyethers, such as fully or partially halogenated polyethers, and copolymers and combinations thereof. Fillers such as metals, carbon fibers, glass fibers and ceramics may be incorporated into the coatings, sleeves or liners. The liner or liners may be on the stent 10, components of the stent 10, and combinations thereof. For example, the liner may be located on the inner surface of the stent 10, or it may be located on the outer surface of the stent 10. The sleeve or liner 26, in part or in total, may be temporary, for example bioabsorbable, biodegradable, and the like, or may be permanent (i.e., not substantially bioabsorbable or biodegradable), for example the above-described biocompatible metals, alloys, polymers and biological materials.

Stent 10 may be treated with a therapeutic agent or agents. "Therapeutic agents", "pharmaceuticals," "pharmaceutically active agents", "drugs" and other related terms may be used interchangeably herein and include genetic therapeutic agents, non-genetic therapeutic agents and cells. Therapeutic agents may be used singly or in combination. A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Non-limiting examples of useful therapeutic agents include, but are not limited to, adrenergic agents, adrenocortical steroids, adrenocortical suppressants, alcohol deterrents, aldosterone antagonists, amino acids and proteins, ammonia detoxicants, anabolic agents, analeptic agents, analgesic agents, androgenic agents, anesthetic agents, anorectic compounds, anorexic agents, antagonists, anterior pituitary activators and suppressants, anthelmintic agents, anti-adrenergic agents, anti-allergic agents, anti-amebic agents, anti-androgen agents, anti-anemic agents, anti-anginal agents, anti-anxiety agents, anti-arthritic agents, anti-asthmatic agents, anti-atherosclerotic agents, antibacterial agents, anticholelithic agents, anticholelithogenic agents, anticholinergic agents, anticoagulants, anticoccidal agents, anticonvulsants, antidepressants, antidiabetic agents, antidiuretics, antidotes, antidyskinetics agents, anti-emetic agents, anti-epileptic agents, anti-estrogen agents, antifibrinolytic agents, antifungal agents, antiglaucoma agents, antihemophilic agents, antihemophilic Factor, antihemorrhagic agents, antihistaminic agents, antihyperlipidemic agents, antihyperlipoproteinemic agents, antihypertensives, antihypotensives, anti-infective agents, anti-inflammatory agents, antikeratinizing agents, antimicrobial agents, antimigraine agents, antimitotic agents, antimycotic agents, antineoplastic agents, anti-cancer supplementary potentiating agents, antineutropenic agents, antiobsessional agents, antiparasitic agents, antiparkinsonian drugs, antipneumocystic agents, antiproliferative agents, antiprostatic hypertrophy drugs, antiprotozoal agents, antipruritics, antipsoriatic agents, antipsychotics, antirheumatic agents, antischistosomal agents, antiseborrheic agents, antispasmodic agents, antithrombotic agents, antitussive agents, anti-ulcerative agents, anti-urolithic agents, antiviral agents, benign prostatic hyperplasia therapy agents, blood glucose regulators, bone resorption inhibitors, bronchodilators, carbonic anhydrase inhibitors, cardiac depressants, cardioprotectants, cardiotonic agents, cardiovascular agents, choleretic agents, cholinergic agents, cholinergic agonists, cholinesterase deactivators, coccidiostat agents, cognition adjuvants and cognition enhancers, depressants, diagnostic aids, diuretics, dopaminergic agents, ectoparasiticides, emetic agents, enzyme inhibitors, estrogens, fibrinolytic agents, free oxygen radical scavengers, gastrointestinal motility agents, glucocorticoids, gonad-stimulating principles, hemostatic agents, histamine H2 receptor antagonists, hormones, hypocholesterolemic agents, hypoglycemic agents, hypolipidemic agents, hypotensive agents, HMGCoA reductase inhibitors, immunizing agents, immunomodulators, immunoregulators, immunostimulants, immunosuppressants, impotence therapy adjuncts, keratolytic agents, LHRH agonists, luteolysin agents, mucolytics, mucosal protective agents, mydriatic agents, nasal decongestants, neuroleptic agents, neuromuscular blocking agents, neuroprotective agents, NMDA antagonists, non-hormonal sterol derivatives, oxytocic agents, plasminogen activators, platelet activating factor antagonists, platelet aggregation inhibitors, post-stroke and post-head trauma treatments, progestins, prostaglandins, prostate growth inhibitors, prothyrotropin agents, psychotropic agents, radioactive agents, repartitioning agents, scabicides, sclerosing agents, sedatives, sedative-hypnotic agents, selective adenosine A1 antagonists, adenosine A2 receptor antagonists (e.g., CGS 21680, regadenoson, UK 432097 or GW 328267), serotonin antagonists, serotonin inhibitors, serotonin receptor antagonists, steroids, stimulants, thyroid hormones, thyroid inhibitors, thyromimetic agents, tranquilizers, unstable angina agents, uricosuric agents, vasoconstrictors, vasodilators, vulnerary agents, wound healing agents, xanthine oxidase inhibitors, and the like, and combinations thereof Useful non-genetic therapeutic agents for use in connection with the present invention include, but are not limited to:

(a) anti-thrombotic agents such as heparin, heparin derivatives, urokinase, clopidogrel, and PPack (dextrophenylalanine proline arginine chloromethylketone);

(b) anti-inflammatory agents such as dexamethasone, prednisolone, corticosterone, budesonide, estrogen, sulfasalazine and mesalamine;

(c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors;

(d) anesthetic agents such as lidocaine, bupivacaine and ropivacaine; [0048]

(e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides;

(f) vascular cell growth promoters such as growth factors, transcriptional activators, and translational promotors;

(g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

(h) protein kinase and tyrosine kinase inhibitors (e.g., tyrphostins, genistein, quinoxalines);

(i) prostacyclin analogs;

(j) cholesterol-lowering agents;

(k) angiopoietins;

(l) antimicrobial agents such as triclosan, cephalosporins, aminoglycosides and nitrofurantoin;

(m) cytotoxic agents, cytostatic agents and cell proliferation affectors;

(n) vasodilating agents;

(o) agents that interfere with endogenous vasoactive mechanisms;

(p) inhibitors of leukocyte recruitment, such as monoclonal antibodies;

(q) cytokines;

(r) hormones;

(s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin;

(t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine);

(u) bARKct inhibitors;

(v) phospholamban inhibitors;

(w) Serca 2 gene/protein;

(x) immune response modifiers including aminoquizolines, for instance, imidazoquinolines such as resiquimod and imiquimod;

(y) human apolioproteins (e.g., AI, AII, AIII, AIV, AV, etc.);

(z) selective estrogen receptor modulators (SERMs) such as raloxifene, lasofoxifene, arzoxifene, miproxifene, ospemifene, PKS 3741, MF 101 and SR 16234;

(aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar;

(bb) prostaglandin E agonists, including PGE2 agonists, such as alprostadil or ONO 8815Ly;

(cc) thrombin receptor activating peptide (TRAP);

(dd) vasopeptidase inhibitors including benazepril, fosinopril, lisinopril, quinapril, ramipril, imidapril, delapril, moexipril and spirapril;

(ee) thymosin beta 4;

(ff) phospholipids including phosphorylcholine, phosphatidylinositol and phosphatidylcholine; and (gg) VLA-4 antagonists and VCAM-1 antagonists.

The non-genetic therapeutic agents may be used individually or in combination, including in combination with any of the agents described herein.

Further examples of non-genetic therapeutic agents, not necessarily exclusive of those listed above, include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Useful genetic therapeutic agents for use in connection with the present invention include, but are not limited to, anti-sense DNA and RNA as well as DNA coding for the various proteins (as well as the proteins themselves), such as (a) anti-sense RNA; (b) tRNA or rRNA to replace defective or deficient endogenous molecules; (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor; (d) cell cycle inhibitors including CD inhibitors, and (e) thymidine kinase ("TK") and other agents useful for interfering with cell proliferation. DNA encoding for the family of bone morphogenic proteins ("BMP's") are also useful and include, but not limited to, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently desirably BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include, but not limited to, viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SP1017 (SUPRATEK), lipids such as cationic lipids, liposomes, lipoplexes, nanoparticles, or microparticles, with and without targeting sequences such as the protein transduction domain (PTD).

Cells for use in connection with the present invention may include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis (antirestenotics). Such agents are useful for the practice of the present invention and include one or more of the following:

(a) Ca-channel blockers including benzothiazapines such as diltiazem and clentiazem, dihydropyridines such as nifedipine, amlodipine and nicardapine, and phenylalkylamines such as verapamil;

(b) serotonin pathway modulators including: 5-HT antagonists such as ketanserin and naftidrofuryl, as well as 5-HT uptake inhibitors such as fluoxetine;

(c) cyclic nucleotide pathway agents including phosphodiesterase inhibitors such as cilostazole and dipyridamole, adenylate/Guanylate cyclase stimulants such as forskolin, as well as adenosine analogs;

(d) catecholamine modulators including α-antagonists such as prazosin and bunazosine, β-antagonists such as propranolol and α/β-antagonists such as labetalol and carvedilol;

(e) endothelin receptor antagonists such as bosentan, sitaxsentan sodium, atrasentan, endonentan;

(f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine;

(g) Angiotensin Converting Enzyme (ACE) inhibitors such as cilazapril, fosinopril and enalapril;

(h) ATII-receptor antagonists such as saralasin and losartin;

(i) platelet adhesion inhibitors such as albumin and polyethylene oxide;

(j) platelet aggregation inhibitors including cilostazole, aspirin and thienopyridine (ticlopidine, clopidogrel) and GP IIb/IIIa inhibitors such as abciximab, epitifibatide and tirofiban;

(k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C;

(l) cyclooxygenase pathway inhibitors such as aspirin, ibuprofen, flurbiprofen, indomethacin and sulfinpyrazone;

(m) natural and synthetic corticosteroids such as dexamethasone, prednisolone, methprednisolone and hydrocortisone;

(n) lipoxygenase pathway inhibitors such as nordihydroguairetic acid and caffeic acid;

(o) leukotriene receptor antagonists;

(p) antagonists of E- and P-selectins;

(q) inhibitors of VCAM-1 and ICAM-1 interactions;

(r) prostaglandins and analogs thereof including prostaglandins such as PGE1 and PG12 and prostacyclin analogs such as ciprostene, epoprostenol, carbacyclin, iloprost and beraprost;

(s) macrophage activation preventers including bisphosphonates;

(t) HMG-CoA reductase inhibitors such as lovastatin, pravastatin, atorvastatin, fluvastatin, simvastatin and cerivastatin;

(u) fish oils and omega-3-fatty acids;

(v) free-radical scavengers/antioxidants such as probucol, vitamins C and E, ebselen, trans-retinoic acid, SOD (orgotein) and SOD mimics, verteporfin, rostaporfin, AGI 1067, and M 40419;

(w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives;

(x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518;

(y) cell motility inhibitors such as cytochalasin B;

(z) antiproliferative/antineoplastic agents including antimetabolites such as purine antagonists/analogs (e.g., 6-mercaptopurine and pro-drugs of 6-mercaptopurine such as azathioprine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin;

(aa) matrix deposition/organization pathway inhibitors such as halofuginone or other quinazolinone derivatives, pirfenidone and tranilast;

(bb) endothelialization facilitators such as VEGF and RGD peptide;

(cc) blood rheology modulators such as pentoxifylline and (dd) glucose cross-link breakers such as alagebrium chloride (ALT-711).

These therapeutic agents may be used individually or in combination, including in combination with any of the agents described herein.

Numerous additional therapeutic agents useful for the practice of the present invention are also disclosed in U.S. Pat. No. 5,733,925 to Kunz, the contents of which are incorporated herein by reference.

A wide range of therapeutic agent loadings may used in connection with the dosage forms of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

In some embodiments, a coating or a sleeve or liner 26 may be disposed on the inner surface of the stent 10, the outer surface of the stent 10, or combinations thereof. For example, as can be seen in FIGS. 3 and 4, the inner portion 12 may include a liner 26 on its inner surface, while the outer portion 14 may not include a liner 26. The incorporation of a liner 26 on the inner surface of the inner segment 12 allows for a smoother flow of fluid or materials through the stent 10, whereas the unlayered outer segment 14 is pressed against the inner surface of a lumen. In this design, the outer segment 14, being unlayered, would anchor better to the lumen wall, because it has been left unlayered, while the inner segment 12 would prevent or reduce tissue ingrowth because it is layered.

The stent 10 alternatively may be embedded, partially or entirely, in the coating sleeve or liner 26. For example, the wires or filaments 20 may be dip-coated in a polymer such as silicone or other polymer.

Further, in some embodiments, only certain regions of the stent 10, such as a flared or tapered distal end 22, may be covered with a liner 26. In addition, the liner 26 may be a tubular sleeve, which may be disposed on the inner or outer surface of the stent 10. Other similar variations and placements of a liner 26 at other locations on the stent 10 are contemplated. Each end may have a different layer than the other, or each may have the same layer.

Methods of introducing and implanting the stent 10 of the present invention are provided herein. Any known implantation methods are suitable for the placement of the stent 10 of the present invention. For example, the stent may be implanted through the use of any known delivery device. The stent 10 is typically inserted through the use of a catheter while the stent 10 is in a collapsed state. In one preferred embodiment, the stent 10 is a self-expanding stent. The stent 10 may be inserted into the inner surface of any bodily lumen, including, for example, the esophageal or an arterial lumen. Once inserted, the stent 10 self-expands, and pushes the wall of the lumen outward, enlarging the region of the lumen in which it is implanted. For example, the implantation site may be at least partially blocked with a tumorous growth, making the passage of bodily fluids or other desired materials therethrough difficult, if not impossible. The stent 10 may be implanted at the site of the growth, and allowed to expand. Expansion opens the blocked lumen, allowing for the passage of fluids or materials therethrough.

As discussed previously, the stent 10 of the present invention may be a dual-layered structure, incorporating two concentrically disposed mesh segments 12 and 14. The stent 10 may, for example, include an inner segment 12 including at least one inner wire, and an outer segment 14 including at least one outer wire. If desired, the outer segment 14 may form a continuous connection with the inner segment 12. The inner segment 12 and the outer segment 14 may be in contact with each other, or they may be spaced apart. Each of the segments 12 and 14 exert an outward force on the lumen, which increases the ability of the stent 10 to resist migration through the lumen. Further, in one embodiment, the outer segment 14 is coated with a material as described above, such as silicone, which may assist in frictional engagement to the inner surface of the lumen. Such coating further aids in the resistance to migration. In other embodiments, the outer segment 14 may include barbs or other components which serve to increase the adherence to the inner surface of the lumen. Thus, the stent 10, after implantation, is adhered to the inner surface of the lumen, and is sufficiently placed so as to resist migration through the lumen. As set forth above, the inner segment 12 and the outer segment 14 may be any desired configuration, including, for example, braided, knitted, twisted, and the like.

In one embodiment of the invention, incorporating the stent wherein the outer segment 14 is inverted over the inner segment 12, aids in the adjustment, removal and/or replacement of the stent 10 after implantation, while still maintaining the high adherence and anti-migration capabilities. The use of the continuous, dual-layered stent 10 in this embodiment allows for the operator to easily remove or replace the stent 10 even after implantation. After implantation, the inner segment 12 may be pulled toward the distal end 22, which serves to constrict the connected outer segment 14, and results in peeling the stent 10 away from the inner surface of the lumen. Since the inner segment 12 is not adhered directly to the lumen, or is at least not as tightly frictionally engaged to the lumen as the dual-layered portion, removal and replacement of the stent 10 is much easier for the operator to accomplish. This is especially true if the inner and outer segments 12 and 14 have different constructs, as peeling may be made easier. The interface area may be made compliant to effectuate removal.

Further, after implantation, the inner segment 12 may be moved in either direction along the axis of the tubular stent 10 (i.e., towards the distal end 22 or towards the inverted end 16), which results in either increasing or decreasing the length of the outer segment 14, respective to the inner segment 12. For example, should the operator wish to decrease the length of the outer segment 14, the operator may pull the inner segment 12 towards the distal end 22 of the stent 10. Pulling the inner segment 12 towards the distal end 22 of the stent 10 results in a portion of the outer segment 14 being constricted and pulled towards the inner segment 12, reducing the length of the outer segment 14. Likewise, the operator may push the inner segment 12 towards the inverted end 16 of the stent 10, which results in the portion of the inner segment 12 being folded back, becoming part of the outer segment 14 of the stent 10. This resizing may take place at one or both ends. Further, the resizing may be accomplished at any time, including days or weeks after implantation as needed. The ability to increase or decrease the axial length of the dual-layered stent 10 in vivo gives the operator a great deal of latitude during implantation.

It may be desired to implant a tubular stent, where the implanted tubular stent is formed of at least two stents joined thereto. In such embodiments, the user may first implant a stent, there the stent includes a first stent body having a generally cylindrical mesh segment. The first stent body is preferably formed of at least one first wire, the first wire forming a plurality of intersecting crossing points to define an open lattice tubular wall as described above. The user may then implant a second stent, where the second stent includes a second stent body having a generally cylindrical mesh segment. As with the first stent, the second stent body is preferably formed of at least one second wire, the second wire forming a plurality of intersecting crossing points to define an open lattice tubular wall. The user may then at least partially connect an end of the first stent body to an end of the second stent body so as to form a multi-layered stent.

While various embodiments of the present invention are specifically illustrated and/or described herein, it will be appreciated that modifications and variations of the present invention may be affected by those skilled in the art without departing from the spirit and intended scope of the invention. Further, any of the embodiments or aspects of the invention as described in the claims or throughout the specification may be used with one and another without limitation.

What is claimed is:

1. A tubular stent comprising:
   a. an inner section comprising at least one first wire, the inner section defined by intersecting crossing points of the at least one first wire; and
   b. a concentric outer section comprising at least one second wire, the outer section defined by intersecting crossing points of the at least one second wire;
   wherein the inner section does not form a continuous connection with the outer section, and
   wherein the concentric outer section is folded over the inner section.

2. The stent of claim 1, wherein the inner section is attached to the outer section.

3. The stent of claim 1, further comprising at least one flared end.

4. A tubular stent comprising:
   an inner section comprising at least one first wire, the inner section defined by intersecting crossing points of the at least one first wire;
   a concentric outer section comprising at least one second wire, the outer section defined by intersecting crossing points of the at least one second wire; and
   at least one flared end;
   wherein the inner section does not form a continuous connection with the outer section, and
   wherein the concentric outer section is folded back over the inner section at an end opposite the flared end.

5. The stent of claim 1, wherein the first and second wires are braided.

6. A tubular stent comprising:
   an inner section comprising at least one first wire, the inner section defined by intersecting crossing points of the at least one first wire; and
   a concentric outer section comprising at least one second wire, the outer section defined by intersecting crossing points of the at least one second wire;
   wherein the inner section does not form a continuous connection with the outer section, and
   wherein the concentric outer section is folded over the inner section;
   wherein the inner and outer sections comprise 8 to 24 wires.

7. The stent of claim 1, further comprising a coating provided on at least one of the inner section or outer section.

8. The stent of claim 7, wherein the coating comprises an active agent.

9. The stent of claim 8, wherein the coating comprises a substantially continuous layer.

10. The stent of claim 1, further comprising at least one additional concentrically disposed section.

11. The stent of claim 1, wherein the concentric outer section is cylindrical.

12. The stent of claim 4, further comprising a coating provided on at least one of the inner section or outer section.

13. The stent of claim 12, wherein the coating comprises an active agent.

14. The stent of claim 13, wherein the coating comprises a substantially continuous layer.

15. The stent of claim 4, further comprising at least one additional concentrically disposed section.

16. The stent of claim 4, wherein the concentric outer section is cylindrical.

* * * * *